US012661006B2

(12) United States Patent
    Zumkehr et al.

(10) Patent No.: US 12,661,006 B2
(45) Date of Patent: Jun. 23, 2026

(54) OPHTHALMIC WORKSTATION

(71) Applicant: Haag-Streit AG, Köniz (CH)

(72) Inventors: Frank Zumkehr, Köniz (CH); Jörg Breitenstein, Köniz (CH); Adrian Zimmermann, Köniz (CH); Fredy Guarriello, Köniz (CH)

(73) Assignee: Haag-Streit AG, Köniz (CH)

( * ) Notice: Subject to any disclaimer, the term of this patent is extended or adjusted under 35 U.S.C. 154(b) by 374 days.

(21) Appl. No.: 18/268,526

(22) PCT Filed: Dec. 21, 2020

(86) PCT No.: PCT/EP2020/087454
    § 371 (c)(1),
    (2) Date: Jun. 20, 2023

(87) PCT Pub. No.: WO2022/135663
    PCT Pub. Date: Jun. 30, 2022

(65) Prior Publication Data
    US 2024/0032791 A1      Feb. 1, 2024

(51) Int. Cl.
    *A61B 3/135* (2006.01)
    *A61B 3/13* (2006.01)

(52) U.S. Cl.
    CPC .............. *A61B 3/135* (2013.01); *A61B 3/132* (2013.01); *A61B 2560/04* (2013.01)

(58) Field of Classification Search
    None
    See application file for complete search history.

(56) References Cited

U.S. PATENT DOCUMENTS

| | | | | | |
|---|---|---|---|---|---|
| 2,622,473 | A | * | 12/1952 | Littmann | A61B 3/135 |
| | | | | | 351/216 |
| 4,187,005 | A | * | 2/1980 | Rosenberger | A61B 3/0075 |
| | | | | | 351/245 |
| 5,382,988 | A | | 1/1995 | Nanjo | |

(Continued)

FOREIGN PATENT DOCUMENTS

| | | |
|---|---|---|
| DE | 10138158 | 2/2003 |
| DK | 1416843 | 3/2009 |

(Continued)

OTHER PUBLICATIONS

Int'l Search Report (Form PCT/ISA/210) conducted in Int'l Appln. No. PCT/EP2020/087454, dated Sep. 16, 2021.

(Continued)

*Primary Examiner* — Sharrief I Broome
*Assistant Examiner* — Journey F Sumlar
(74) *Attorney, Agent, or Firm* — GREENBLUM & BERNSTEIN, P.L.C.

(57) ABSTRACT

The ophthalmic workstation comprises a table having a top surface, a base unit mounted to the table, a microscope, and a headrest. The base unit includes an X-displacement stage, a Z-displacement stage, and a platform mounted to the X-displacement stage and the Z-displacement stage. The microscope is mounted to the platform. The table comprises an opening in its top surface. An embedded section of the base unit is located, at least in part, in this recess or opening. The headrest is mounted to a headrest section of the base unit, which projects laterally over an edge of the table.

16 Claims, 3 Drawing Sheets

(56)         References Cited

U.S. PATENT DOCUMENTS

| | | | |
|---|---|---|---|
| 5,387,952 A | 2/1995 | Byer | |
| 6,208,460 B1 * | 3/2001 | Degenhardt | ....... G02B 21/0012 |
| | | | 359/387 |
| 7,338,172 B2 | 3/2008 | Yoshimura et al. | |
| 7,515,321 B2 | 4/2009 | Mimura et al. | |
| 7,819,528 B1 | 10/2010 | Dudee | |
| 2004/0114107 A1 * | 6/2004 | Mimura | ................... A61B 3/10 |
| | | | 351/208 |
| 2014/0063448 A1 * | 3/2014 | Nakahara | ............. A61B 3/0083 |
| | | | 351/246 |
| 2016/0374549 A1 * | 12/2016 | Xue | .................... A61B 3/0083 |
| | | | 351/221 |
| 2018/0303335 A1 * | 10/2018 | Xue | .................... A61B 3/0033 |
| 2019/0282091 A1 | 9/2019 | Matsunobu | |
| 2020/0245866 A1 * | 8/2020 | Bartelen | ............... A61B 3/135 |

FOREIGN PATENT DOCUMENTS

| | | |
|---|---|---|
| EP | 3530228 | 8/2019 |
| JP | 2012-231936 | 11/2012 |

OTHER PUBLICATIONS

Int'l Written Opinion (Form PCT/ISA/237) conducted in Int'l Appln. No. PCT/EP2020/087454, dated Sep. 16, 2021.

* cited by examiner

OPHTHALMIC WORKSTATION

TECHNICAL FIELD

The invention relates to an ophthalmic workstation including a table, a base mounted to the table, and an ophthalmic microscope mounted to the base.

BACKGROUND ART

U.S. Pat. No. 751,321 describes an ophthalmic device to be placed on a table to form an ophthalmic workstation. It has a base and an ophthalmic microscope mounted to the base. The base provides for a displacement of the microscope along the horizontal directions parallel to the top surface of the table.

DISCLOSURE OF THE INVENTION

The problem to be solved by the present invention is to provide a workstation of this type that is more convenient to use.

This problem is solved by the workstation of claim 1.

Accordingly, the invention relates to an ophthalmic workstation comprising at least the following elements:

A table having a top surface.

A base unit mounted to the table. This is the part that facilitates the horizontal displacement of the microscope in respect to the table. It comprises at least the following elements:

a) An X-displacement stage.

b) A Z-displacement stage.

c) A platform mounted to the X-displacement stage and the Z-displacement stage. This platform is displaceable along the X- and Z-directions. These directions are perpendicular to each other and extend parallel to the top surface of the table.

A microscope mounted to the platform: Hence, by means of the platform, the microscope can be displaced along the X- and Z-directions.

The table comprises an opening in its top surface, which may e.g. formed by a recess or through-opening in its top board. The base unit comprises an embedded section located in said opening below the top surface. This allows to reduce the height by which the base unit projects over the top surface of the table, which makes the workstation easier to operate.

The workstation may comprise a headrest mounted to the base unit for supporting the patient's head. In that case, the base unit may comprise a headrest section for holding the headrest. This headrest section may horizontally project over (i.e. extend over) an edge of the table.

Further, the headrest section of the base unit may have two support sections. The base unit further has a recessed section between the support sections, with the outer edge of the recessed section being closer to the (closest) edge of the table than the outer edges of the support sections. In that case, the headrest comprises two vertical, spaced-apart support columns mounted in the support sections. In this design, the recessed section forms a bay that may accommodate the patient's chest.

The recessed section may form part of the headrest section, i.e. it may also horizontally project over the edge of the table but less so than the support sections.

The base unit may be partially embedded in the table in the sense that it has a cover section above the embedded section and above the top surface of the table.

In this case, the cover section may form a ledge horizontally projecting over at least three sides of the embedded section. This ledge can be used to cover the gap between the embedded section and the surrounding top board of the table.

The workstation may further comprise at least the following elements:

An access opening above the platform, e.g. in the cover section: The platform is movable, in respect to the access opening, along the X- and directions, between a plurality of working positions.

A microscope support connected to the platform and through the access opening: This element supports the microscope.

A shield connected to the support: This shield covers the access opening by being adjacent to the access opening, and it is large enough to cover the access opening in all of the working positions of the platform.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Definitions

Figures 1, 2:
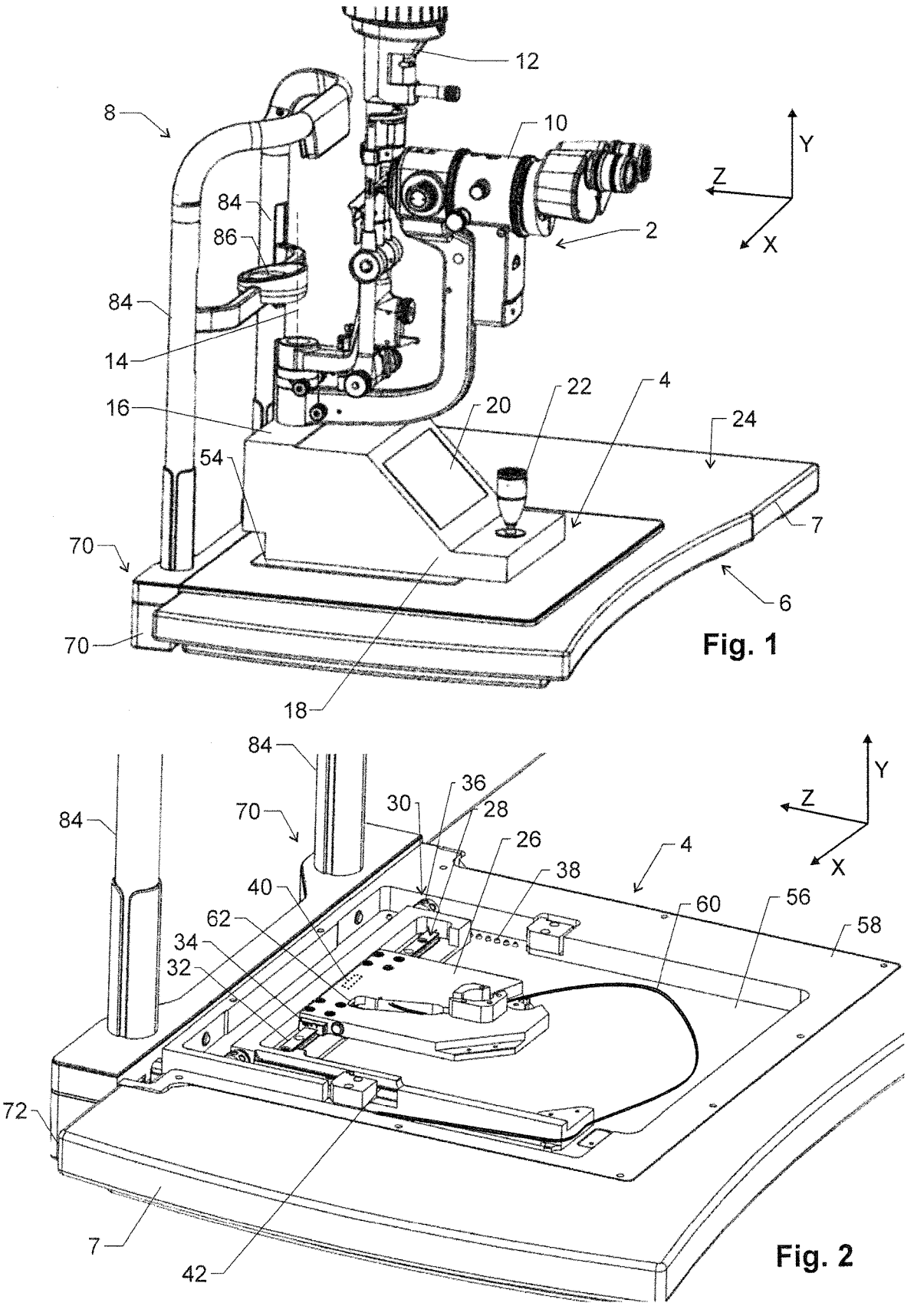
FIG. 1 shows an embodiment of a workstation with an ophthalmic microscope.
FIG. 2 shows the base unit with the cover section removed.

Any expression referring to a direction of gravity are to be understood for the normal "operating position" of the workstation. In particular:

A "horizontal" direction as used herein is any direction parallel to the top surface of the table.

A "vertical" direction is any direction perpendicular to the top surface of the table.

Expressions such as "above", "below", "top" or "down" are in reference to the normal direction of gravity. Hence, by definition, the top surface of the table is above the embedded section of the base unit, but it is below the microscope.

Overview

The figures shown an embodiment of a workstation comprising an ophthalmic microscope 2. The microscope is only shown in FIG. 1.

Microscope 2 is mounted to a base unit 4, which is at least partially embedded in a table 6. The workstation further includes a headrest 8 for the patient to place his/her chin and forehead in.

Table 6 is a piece of furniture typically mounted in the ophthalmologist's practice. It advantageously has a height of at least 60 cm. It typically comprises a top board 7 mounted to a suitable support, such as legs or a chest of drawers (not shown in the figures).

In the shown example, microscope 2 is a slit lamp microscope having a microscope unit 10 and a slit lamp 12, both of which are pivotal in respect to a microscope support 16 about a vertical pivot axis 14.

Microscope 2 comprises, as mentioned, a microscope support 16, which has a foot section 18. It may e.g. carry a display 20 and a joystick 22, even though display 20 may also be arranged elsewhere.

The user can displace microscope support 16 along the horizontal X and Z directions parallel to the top surface 24 of table 6, e.g. by operating joystick 22.

In this context, direction Z is the direction of the optical axis of the microscope in its central position, and direction X is the horizontal direction X perpendicular to direction Z. Direction Y is the vertical direction.

Base Unit

Base unit 4 supports microscope 2 in a horizontally displaceable manner and connects it to table 6.

Figure 3:
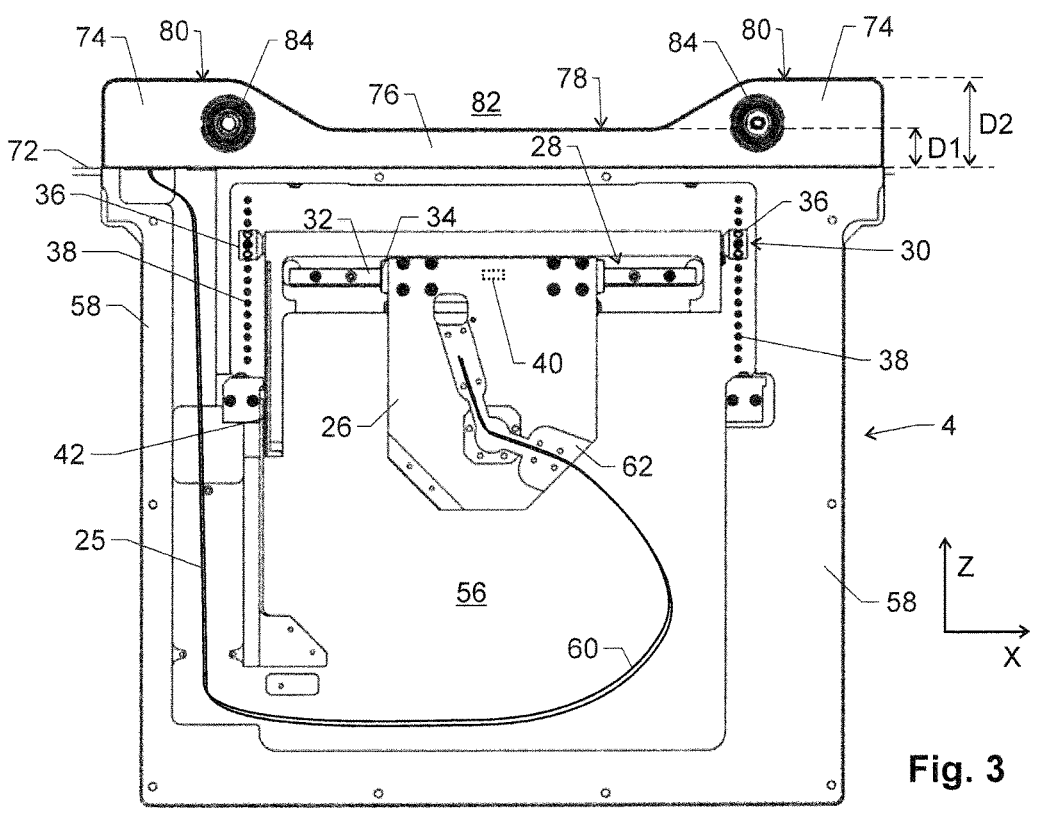
FIG. 3 is a top view of FIG. 2.
Figure 4:
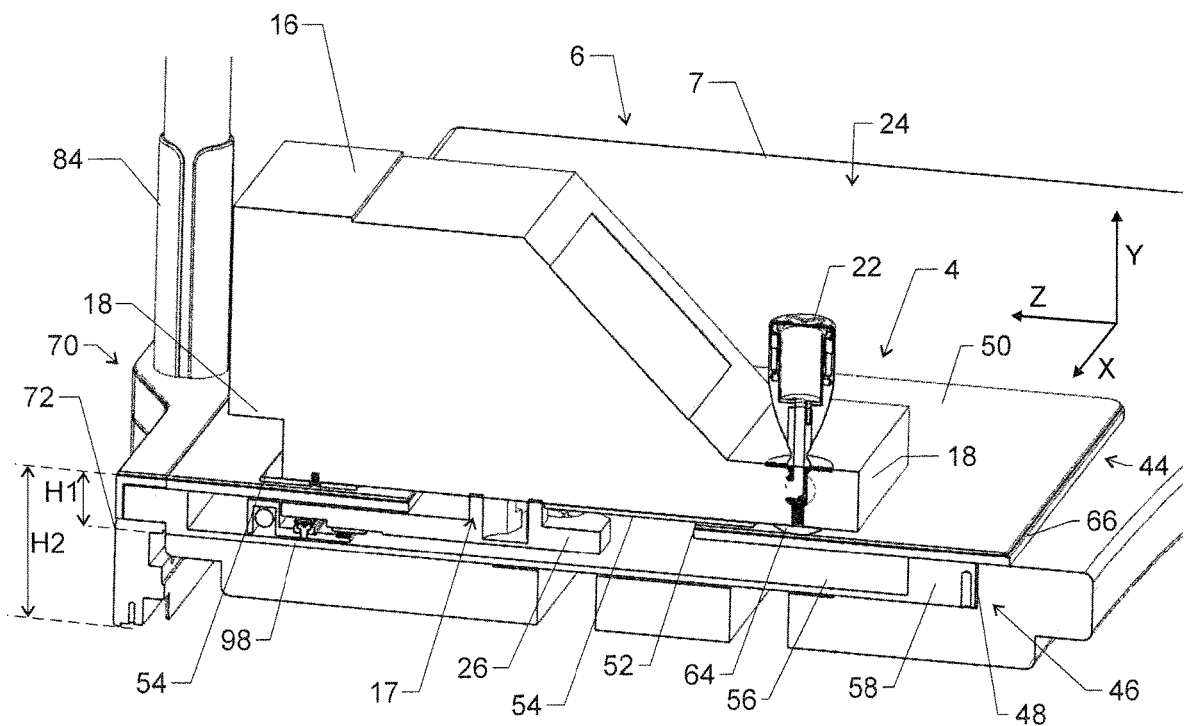
FIG. 4 is a sectional view along a central, vertical plane extending through the joystick and being parallel to the Z-direction.

As shown in FIGS. 2-4, it comprises a platform 26, which is connected to foot section 18 and therefore to microscope support 16. It is displaceable in the directions X and Z. For this purpose, platform 26 is mounted to an X-displacement stage 28, which is in turn connected to a Z-displacement stage 30.

As best seen in FIGS. 2 and 3, X-displacement stage 28 comprises a guide rail 32, which is engaged by a linear bearing 34 of platform 26.

Z-displacement stage 30 comprises two cogwheels 36 running along two linear tracks of projections 38. The cogwheels 36 are mounted to guide rail 32, and the tracks are mounted to the bottom of base unit 4.

A first sensor 40 measures the absolute or relative position (along direction X) of platform 26 in respect to guide rail 32, and a second sensor 42 measures the absolute or relative position (along direction 1) of guide rail 32 in respect to table 6.

As is best seen in FIG. 4, base unit 4 has a cover section 44 and an embedded section 46 located beneath and fixedly connected to cover section 44. By definition, cover section 44 is located higher than top surface 24 of table 6 and embedded section 46 is located lower than top surface 24 of table 6.

Embedded section 46 is arranged in an opening 48 in top surface 24, i.e. it is arranged within or in part even beneath the top board 7 of table 6.

Advantageously, embedded section 46 includes at least one of, in particular all of: X-displacement stage 28, Z-displacement stage 30, and/or a platform 26. Top section 44 comprises, in the shown embodiment, a cover plate 50 with an access opening 52. Cover plate 50 is stationary in respect to table 6, i.e. it does not move when microscope 2 is moved along directions X or Z.

Microscope support 16 is connected to platform 26 through access opening 52 by means of connecting parts 17. Access opening 52 is large enough to permit a horizontal movement of microscope support 16 to all desired X- and Z-working-positions.

A shield 54, which is horizontally movable with the microscope, and which may be formed as a separate part or as an integral part of foot section 18, is connected to microscope support 16. It is located adjacent to access opening 52 and large enough to cover access opening 52 for all X- and Z-working-positions of microscope 2. "Adjacent", in this context, is to be understood such that the periphery of shield 54 is at the vertical level of the surface surrounding access opening 52.

Platform 26 is arranged in a chamber 56, which is surrounded by a frame 58 of embedded section 46 of base unit 4. Frame 58 is stationary in respect to table 6.

Advantageously, and as shown in FIGS. 2 and 3, cabling 60 is led through chamber 56, an opening 62 in platform 26, and microscope support 16, thereby protecting it from access and hiding it from the user.

Joystick 22 is connected to foot section 18. It is pivotal about the horizontal directions X and Z, and it has a foot 64 resting against cover plate 50 (FIG. 4). It carries at least part of the weight of microscope 2 for good frictional contact.

Tilting joystick 22 allows to displace the microscope in directions X and Z.

Cover section 44 forms a ledge 66, advantageously as a horizontal extension of cover plate 50. It horizontally projects over embedded section 46 of base is unit 4 along the Z-direction towards the operator of the workstation as well as on both sides along the X-direction. As mentioned, it covers any gap between table 6 and embedded section 46, thereby allowing for a larger clearance between these parts.

Headrest

Base unit 4 comprises a headrest section 70 for holding headrest 8. Headrest section 70 extends horizontally from embedded section 46 and projects, along direction Z, towards the patient, over an edge 72 of table 6.

As best can be seen in FIG. 3, headrest section 70 comprises two support sections 74, with a recessed section 76 between them.

The outer edge 78 of recessed section 76 is closer to the closest edge 72 of table 6 than the outer edges 80 of the support sections 74. In other words, and, as shown in FIG. 3, the distance D1 between outer edge 78 and table edge 72 is smaller than the distance D2 between the outer edges 80 and table edge 72. Advantageously, D2–D1 is larger than 3 cm.

Thus, a bay 82 is formed for receiving the patient's chest section.

Headrest 8 comprises two spaced-apart support columns 84, each of which is mounted in one of the support sections 74.

Figure 5:
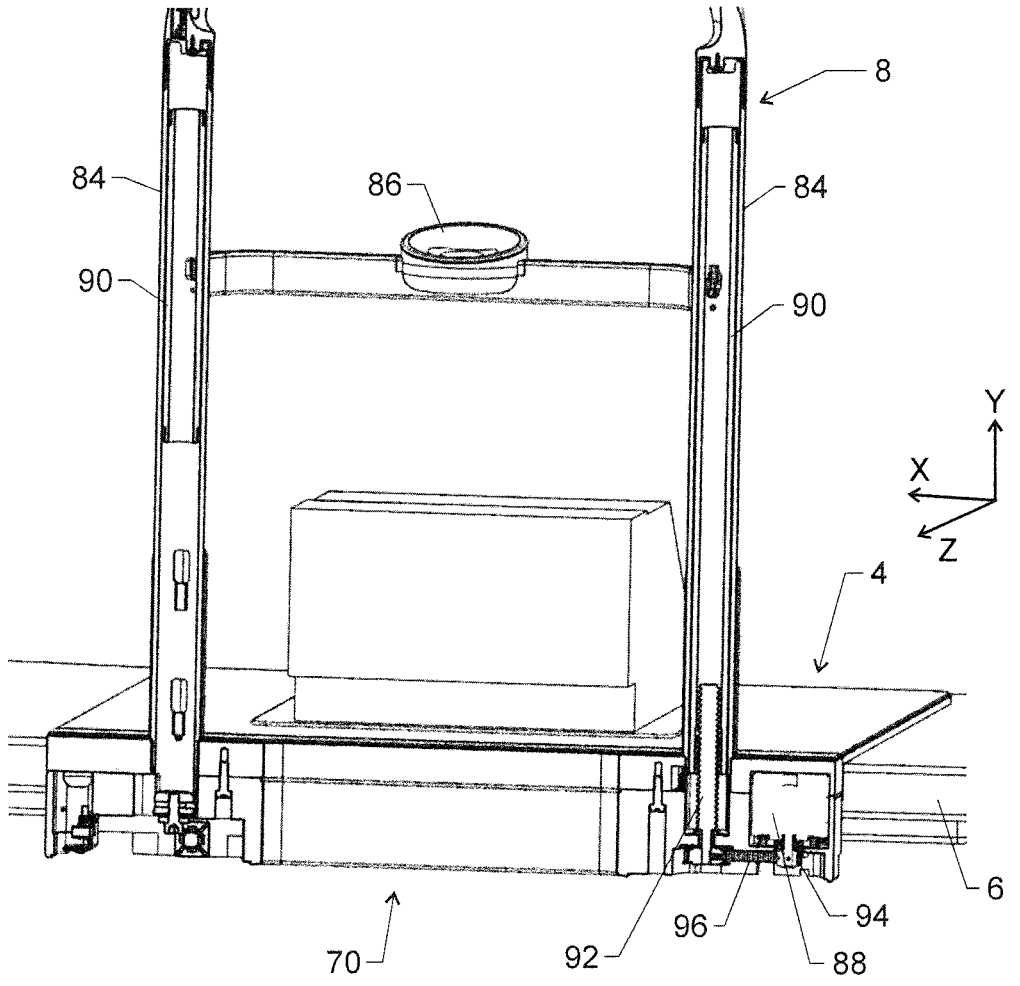
FIG. 5 is a sectional view along a vertical plane extending through the headrest supports.

As best seen in FIG. 5, a chin rest 86 is arranged on the support columns 84 for the patient to rest his chin on.

Chin rest 86 is vertically displaceable by n means of a chin rest drive 88.

In the shown embodiment, chin rest drive 88 is located in headrest section 70 of base unit 4.

Chin rest 86 is connected to two sliders 90 displaceably y arranged within the support columns 84.

Chin rest drive 88 drives a threaded drive member 92, which is also arranged in one of the support columns 84. When operating, chin rest drive 88 rotates threaded drive member 92 about its vertical axis.

Threaded drive member 92 e.g. has an outer threading that engages an inner threading of one of the sliders 90. Thus, by rotating threaded drive member 92, this slider 90 and therefore chin rest 86 can be displaced vertically.

In the embodiment of FIG. 5, headrest drive 88 has a shaft 94 rotatable about a vertical axis and is connected to threaded drive member 92 by means of a belt 96 or by means of a cogwheel coupling.

As shown in FIG. 4, the maximum height HT of embedded section 46 is advantageously smaller than the maximum height H2 headrest section 70, advantageously by at least 20% Designing headrest section 70 to be higher than the embedded section 46 allows to minimize the depth of the opening in table 6 while still providing a robust anchoring of the headrest and/or ample room for chin rest drive 88.

NOTES

In the embodiments above, frame 58 is a part separate from cover plate 50, with the two parts e.g. connected by means of screws.

A bottom 98 (see FIG. 4) of embedded section 46 may be directly connected to frame 58. In the shown example, bottom 98 is integrally connected to frame 58.

In an alternative embodiment, frame 58 may be integrally connected to cover plate 50 and/or at least to ledge 66. This facilitates designs where cover plate 50 or at least ledge 66 can be very thin. In that case, bottom 98 may e.g. be screwed to frame 58.

Hence, in an advantageous embodiment, the invention relates to a workstation where embedded section 46 comprises a frame 58 integrally connected to ledge 66 of cover section 44.

In any embodiment, bottom 98 may also at least be partially dispensed with and e.g. only be located below cogs 38.

While there are shown and described presently preferred embodiments of the invention, it is to be distinctly understood that the invention is not limited thereto but may be otherwise variously embodied and practiced within the scope of the following claims.

The invention claimed is:

1. An ophthalmic workstation comprising:
a table having a top surface,
a base unit mounted to said table, with said base unit comprising:
a) an X-displacement stage,
b) a Z-displacement stage,
c) a platform mounted to said X-displacement stage and said Z-displacement stage and being displaceable horizontally along perpendicular X- and Z-directions parallel to the top surface,
a microscope mounted to said platform,
wherein the table comprises an opening in the top surface and wherein the base unit comprises an embedded section located in the opening below the top surface, and
wherein the platform is arranged in a chamber of the base unit.

2. The workstation of claim 1, further comprising a headrest mounted to the base unit, wherein said base unit comprises headrest section holding the headrest and projecting horizontally over an edge of the table.

3. The workstation of claim 2, wherein
said headrest section comprises two support sections, and
the base unit has a recessed section between the support sections, with an outer edge of the recessed section being closer to the edge of the table than outer edges of the support sections, and
said headrest comprises two spaced-apart support columns mounted in the support sections.

4. The workstation of claim 3, wherein the recessed section forms part of the headrest section.

5. The workstation of claim 3, wherein the headrest comprises a chin rest displaceably mounted to the support columns and a chin rest drive connected to displace the chin rest in a vertical direction.

6. The workstation of claim 5, wherein the chin rest drive is located in the headrest section.

7. The workstation of claim 5, comprising, in at least one of the support columns, a threaded drive member extending along the support column engaging a slider arranged within the support column, wherein the slider is connected to the chin rest.

8. The workstation of claim 1, wherein said base unit has a cover section above the embedded section, wherein the cover section is arranged above the top surface of the table.

9. The workstation of claim 8, wherein the cover section forms a ledge horizontally projecting over at least three sides of the embedded section.

10. The workstation of claim 9, wherein said embedded section comprises a frame that is integrally connected to the ledge.

11. The workstation of claim 1, wherein the chamber is arranged in the embedded section.

12. The workstation of claim 1, wherein cabling for the microscope extends through the chamber, the platform, and a microscope support, wherein the microscope support is connected to the platform.

13. An ophthalmic workstation comprising:
a table having a top surface,
a base unit mounted to said table, with said base unit comprising:
a) an X-displacement stage,
b) a Z-displacement stage,
c) a platform mounted to said X-displacement stage and said Z-displacement stage and being displaceable horizontally along perpendicular X- and Z-directions parallel to the top surface,
a microscope mounted to said platform, wherein the table comprises an opening in the top surface and wherein the base unit comprises an embedded section located in the opening below the top surface, and
a headrest mounted to the base unit, wherein said base unit comprises a headrest section holding the headrest and projecting horizontally over an edge of the table,
wherein the embedded section is connected to the headrest section of the base unit, wherein a maximum height of the embedded section is smaller than a maximum height of the headrest section.

14. The workstation of claim 13, wherein the maximum height of the embedded section is at least 20% smaller than the maximum height of the headrest section.

15. An ophthalmic workstation, comprising:
a table having a top surface,
a base unit mounted to said table, with said base unit comprising:
a) an X-displacement stage,
b) a Z-displacement stage,
c) a platform mounted to said X-displacement stage and said Z-displacement stage and being displaceable horizontally along perpendicular X- and Z-directions parallel to the top surface,
a microscope mounted to said platform,
wherein the table comprises an opening in the top surface and wherein the base unit comprises an embedded section located in the opening below the top surface,
an access opening above the platform, wherein said platform is movable between a plurality of working positions in respect to the access opening along the X- and Z-directions,
a microscope support connected to the platform through the access opening, and
a shield connected to the microscope support, wherein said shield is adjacent to the access opening and large enough to cover the access opening in all of said working positions.

16. An ophthalmic workstation, comprising:

a table having a top surface, a base unit mounted to said table, with said base unit comprising:

a) an X-displacement stage, b) a Z-displacement stage, c) a platform mounted to said X-displacement stage and said Z-displacement stage and being displaceable horizontally along perpendicular X- and Z-directions parallel to the top surface, a microscope mounted to said platform, wherein the table comprises an opening in the top surface and wherein the base unit comprises an embedded section located in the opening below the top surface, and wherein the embedded section comprises at least one of the X-displacement stage and the Z-displacement stage.

* * * * *